United States Patent
Shekhar

(10) Patent No.: US 11,017,906 B2
(45) Date of Patent: May 25, 2021

(54) MACHINE LEARNING MODELS IN LOCATION BASED EPISODE PREDICTION

(71) Applicant: Amino, Inc., San Francisco, CA (US)

(72) Inventor: Shashank Shekhar, San Francisco, CA (US)

(73) Assignee: Amino, Inc., San Francisco, CA (US)

( * ) Notice: Subject to any disclaimer, the term of this patent is extended or adjusted under 35 U.S.C. 154(b) by 911 days.

(21) Appl. No.: 15/717,846

(22) Filed: Sep. 27, 2017

(65) Prior Publication Data

US 2018/0268320 A1     Sep. 20, 2018

Related U.S. Application Data

(60) Provisional application No. 62/473,861, filed on Mar. 20, 2017, provisional application No. 62/516,027, filed on Jun. 6, 2017.

(51) Int. Cl.
| | | |
|---|---|---|
| *G16H 50/70* | (2018.01) | |
| *G06F 19/00* | (2018.01) | |
| *G06N 7/00* | (2006.01) | |
| *G16H 10/60* | (2018.01) | |
| *G06N 20/00* | (2019.01) | |
| *G16H 40/20* | (2018.01) | |

(52) U.S. Cl.
CPC ........... *G16H 50/70* (2018.01); *G06F 19/328* (2013.01); *G06N 7/005* (2013.01); *G06N 20/00* (2019.01); *G16H 10/60* (2018.01); *G16H 40/20* (2018.01)

(58) Field of Classification Search
CPC ........ G16H 50/70; G16H 40/20; G16H 10/60; G06N 20/00; G06N 7/005; G06F 19/328
See application file for complete search history.

(56) References Cited

U.S. PATENT DOCUMENTS

| | | | | |
|---|---|---|---|---|
| 2012/0047105 A1* | 2/2012 | Saigal | ..................... | G06F 19/00 706/52 |
| 2012/0259662 A1* | 10/2012 | Vanderzee | ............. | G16H 70/20 705/4 |
| 2018/0107995 A1* | 4/2018 | Krongrad | ........... | G06Q 10/0875 |

OTHER PUBLICATIONS

Chen et al. "How Should the Hospital Assign Service Volume to Private Payers Optimally?" IEEE EM, 2014, pp. 646-655.*
Hadley et al. "Seeking the Just Price: Constructing Relative Value Scales and Fee Schedules", Annals of Internet Medicine, 1987, pp. 461-466.*

* cited by examiner

*Primary Examiner* — Li Wu Chang
(74) *Attorney, Agent, or Firm* — Perkins Coie LLP

(57) ABSTRACT

The disclosed embodiments include a method performed by server computer(s). The method includes obtaining private healthcare insurance claims data and public healthcare procedure code data from one or more data source(s), generating a model based the training data, and determining a multiplier for each of the many facilities based on the model. The model provides predictive results for variability between healthcare facilities thereby enabling consumer research in light of considerations in facility variability. The multiplier is indicative of a value used to scale the public healthcare procedure code data for a facility such that a healthcare service associated with the facility can be estimated based on the multiplier.

25 Claims, 11 Drawing Sheets

FIG. 4F

MACHINE LEARNING MODELS IN LOCATION BASED EPISODE PREDICTION

CROSS-REFERENCE TO CO-PENDING APPLICATIONS

This patent application claims the benefit of U.S. provisional patent application Ser. No. 62/473,861, filed Mar. 20, 2017, and U.S. provisional patent application Ser. No. 62/516,027, filed Jun. 6, 2017, the entirety of each of these applications are incorporated herein by this reference thereto.

TECHNICAL FIELD

The disclosed teachings relate to data driven predictive models and decision making. In particular, the disclosed teachings relate to techniques for predicting variability of healthcare episodes across a number of healthcare facilities.

BACKGROUND

Existing healthcare systems involve numerous interconnected subsystems used to collectively offer and deliver diverse services to consumers. The complexity of the healthcare system will not change in the foreseeable future because it serves a large population of consumers with unique, complex, and diverse needs. The consumers use various resources to research healthcare information and manage their individual healthcare profiles. For example, an individual can access an online portal via a desktop computer or smartphone to research information and maintain a personal profile. This online portal can include tools for researching information related to medical conditions and searching for local doctors that specialize in treating those medical conditions.

Consumers would like to conduct research in light of considerations in facility variability. Unfortunately, this variability is not transparent to consumers. For example, existing healthcare systems do not have central sources for users to search for healthcare costs by any combination of procedures, insurance, healthcare providers, geographic locations, and the like. Instead, healthcare cost information is unavailable or fragmented across disparate data sources. As a result, users cannot make informed decisions about obtaining services at known prices because this information does not exist in any readily accessible form.

A given episode of healthcare including any particular procedure can depend largely on a particular healthcare provider and the terms of a patient's particular insurer. As a result, patients seeking the same procedure from a healthcare provider may be subjected to different costs.

SUMMARY

The disclosed embodiments include a method performed by server computer(s). The method includes obtaining private healthcare insurance claims data and public healthcare fee schedule data from one or more data source(s), generating a model based on a combination of the private healthcare insurance claims data and the public healthcare fee schedule data, and determining a multiplier for each of many facilities based on the model. The multiplier is indicative of a value used to scale the public healthcare fee schedule for a facility such that a cost for a healthcare service associated with the facility can be estimated based on the multiplier.

Other aspects of the technique will be apparent from the accompanying Figures and Detailed Description.

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 4F illustrates a graphical interface for personalizing an estimate cost according to some embodiments of the present disclosure;

DETAILED DESCRIPTION

Figure 1:
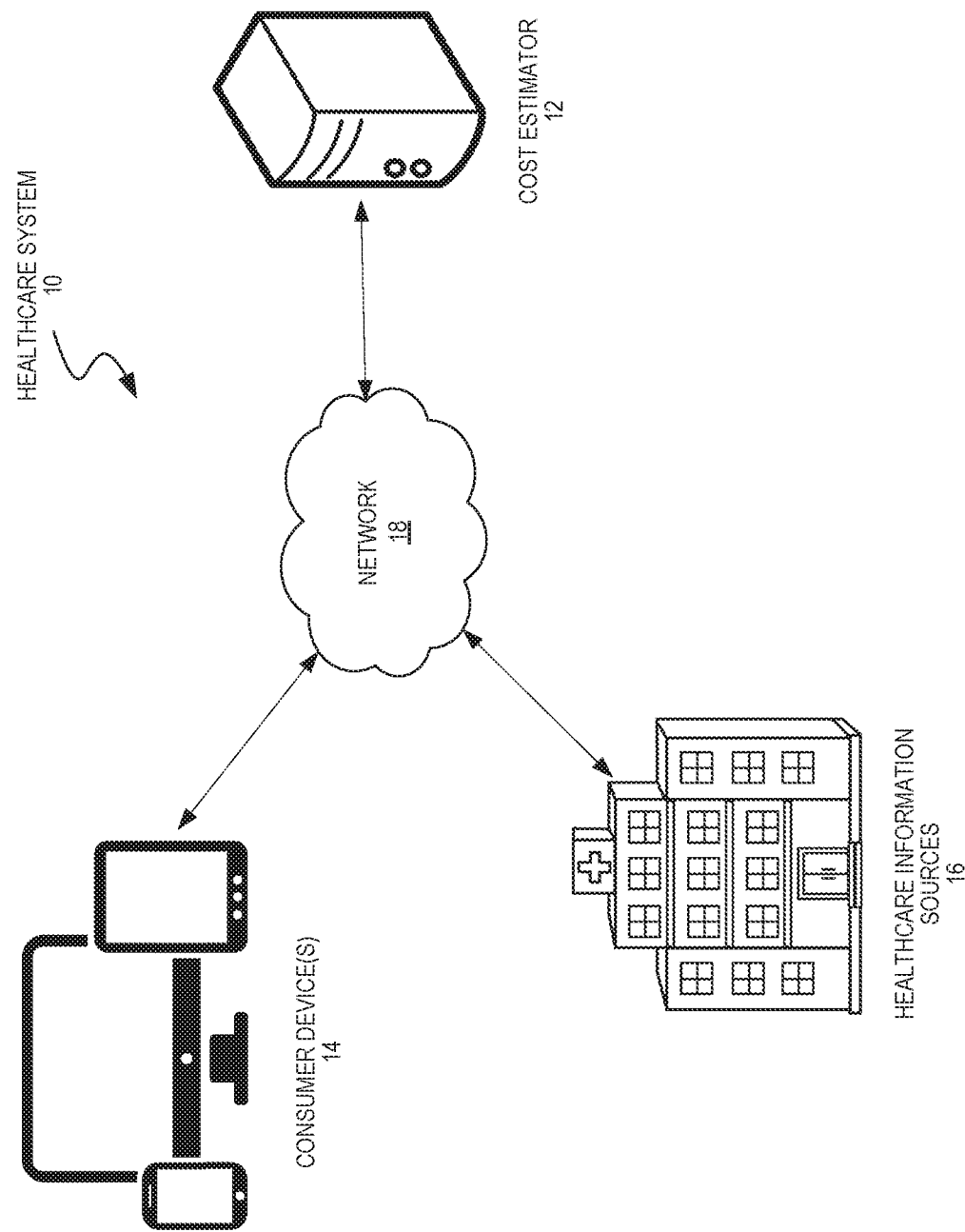
FIG. 1 is a high-level block diagram illustrating a healthcare system according to some embodiments of the present disclosure.

The embodiments set forth below represent the necessary information to enable those skilled in the art to practice the embodiments, and illustrate the best mode of practicing the embodiments. Upon reading the following description in light of the accompanying figures, those skilled in the art will understand the concepts of the disclosure and will recognize applications of these concepts that are not particularly addressed here. It should be understood that these concepts and applications fall within the scope of the disclosure and the accompanying claims.

The purpose of terminology used herein is only for describing embodiments and is not intended to limit the scope of the disclosure. Where context permits, words using the singular or plural form may also include the plural or singular form, respectively.

As used herein, unless specifically stated otherwise, terms such as "processing," "computing," "calculating," "determining," "displaying," "generating," or the like, refer to actions and processes of a computer or similar electronic computing device that manipulates and transforms data represented as physical (electronic) quantities within the computer's memory or registers into other data similarly represented as physical quantities within the computer's memory, registers, or other such storage medium, transmission, or display devices.

As used herein, terms such as "connected," "coupled," or the like, refer to any connection or coupling, either direct or indirect, between two or more elements. The coupling or connection can be physical, logical, or a combination thereof.

As used herein, the term "service" may refer to a healthcare related service or procedure provided by a healthcare provider to a patient. Examples include diagnoses or treatments performed by a doctor or performed at a facility such as a hospital.

As used herein, the term "provider" may refer to an entity that provides healthcare related services. Examples include a doctor, nurse, insurance carrier, practice group, facility, healthcare computer network service, or the like.

As used herein, the terms "consumer" or "patient" may refer to a user who receives services from a provider or who may use the disclosed technology. Furthermore, the term "user" may be a person or machine.

The disclosed embodiments generally relate to solving the problems faced by consumers seeking to know the cost of a healthcare service based on incomplete or fragmented information contained in healthcare systems. The inability to reliably predict costs estimates is increasingly problematic as healthcare costs continue to grow. That is, insurance premiums and deductibles continue increasing yet consumers do not have access to accurate or even interpretable cost estimates that would help them make informed decisions about their healthcare service needs. As a result, users are simply inadequately informed about the costs and cannot make informed decisions when selecting a provider for a particular procedure.

Estimating cost for healthcare services is challenging because of the high dimensionality of healthcare data (e.g., service codes, facilities, insurers), noise (e.g., medical coding is predominantly a manual process), missing data (e.g., a service may include an unrecorded procedure), and external validation is sparse (because this problem is challenging). Hence, healthcare data is interdependent, sparse, and inconsistent. The disclosed embodiments can deal with these challenges to provide accurate, interpretable, and useful cost estimates that are easy to explain to consumers.

The disclosed embodiments overcome these drawbacks by estimating costs of healthcare services and making the estimates available to users. The disclosed embodiments provides transparency into healthcare costs by using existing healthcare related data to formulate cost estimates for healthcare services under one or more constraints. For example, the disclosed technology can estimate a consumer's out-of-pocket costs for a particular procedure performed by a particular healthcare provider under a particular insurance policy based on incomplete or fragmented healthcare related data stored in a healthcare system.

The cost estimates can be based on data contained in one or more data stores that may be accessible over one or more computer networks. In some embodiments, the data used to predict estimate costs ("estimation dataset") can include or be limited to insurance claim records. An insurance claim record may include information related to a patient, healthcare providers, healthcare services, and the like. Accordingly, the data stores can include numerous healthcare claim records. The healthcare claim records can represent claims that range a span of years (e.g., dated 5 years back) and include information for a large population of patients (e.g., over 200 million patients) and a large population of healthcare providers (e.g., 900,000 doctors).

The estimation dataset includes a necessary and sufficient amount of healthcare related data to predict costs estimates for healthcare services. The estimation dataset is not readily available as interpretable accurate data contained in a single central data store. Instead, the estimation dataset may be fragmented and distributed across multiple data stores. Hence, users cannot simply retrieve cost estimates from any data store. In some embodiments, the estimation dataset is collected from disparate data sources and synthesized to predict the healthcare cost estimates. Further, in some embodiments, the collected estimation dataset can be anonymized to protect the privacy of patients and providers.

The disclosed technology is not simply a process for estimating a cost based on data collected from different sources because readily interpretable costs for healthcare services is not available in any data sources. Instead, predicting a cost estimate for a healthcare service involves understanding healthcare services and the structure and content of medical bills. For example, a particular service may involve one or more service codes that may be indicated in a medical bill. In some embodiments, service or procedure codes may be considered interchangeable with a particular cost/amount associated with a given healthcare facility.

In some embodiments, the disclosed technology can collect and parse incomplete or fragmented healthcare related information from one or more data sources to create an estimation dataset that defines one or more episodes of care. An episode of care can include one or more service codes and a price for each service code. A cost estimate for a healthcare service can be predicted as a function of an episode of care. Then, for example, a user can input a particular service into a user interface used to predict a cost estimate. The user interface can display one or more predicted costs estimates. The user can select a particular cost estimate to present another display of additional information used to predict that particular cost estimate. As such, a user can easily determine a cost estimate for a healthcare service.

In some embodiments, different types of data sets are used to estimate costs. For example, data from combinations of insurance claim records, payment records, or fee schedule records can be collected and combined to form an estimation dataset. The insurance claim records may include information indicative of interactions between patients and providers. The payment records may include information indicative of the portions of fees paid by insurers to healthcare providers. The fee schedule records may include a schedule of fees paid by an entity. A combination of data from the claims records, payment records, or fee schedule records can be input to an algorithm used to generate one or more models that identify episodes of care. The estimate costs of healthcare services can then be predicted based on the episodes of care.

For example, a model can be generated by applying Bayesian regression on data from private insurance claim records and a public fee schedule such as a fee schedule from the Centers for Medicare & Medicaid Services (CMS). The data can include pairs of facilities and insurers, and the model can be a linear model. Episodes of care can be identified from the model and used to determine estimate costs for healthcare procedures. In some embodiments, a representative episode-level cost can be computed as a frequency weighted combination of individual episode costs. As such, the outputs of this process can help users choose healthcare providers based on the estimate costs of healthcare services. For example, users can identify a doctor for a procedure, estimate the cost for a particular procedure performed by a particular doctor, and estimate the cost for undergoing a particular procedure at a particular facility.

FIG. 1 is a block diagram of a healthcare system 10 operable to estimate costs of healthcare procedures according to some embodiments of the present disclosure. The healthcare system 10 can generate cost estimates for procedure per provider. The cost estimates can be made available to consumers and providers to make more informed healthcare decisions. The healthcare system 10 includes components such as one or more servers of a cost estimator 12, consumer devices 14, and healthcare information sources 16, all interconnected over a network 18 such as the Internet.

The network 18 may include any combination of private, public, wired, or wireless portions. The data communicated over the network 18 may be encrypted or unencrypted at various locations or along different portions of the network 18. Each component of the healthcare system 10 may include combinations of hardware and/or software to process data, perform functions, communicate over the network 18, and the like. For example, any component of the healthcare system 10 may include a processor, memory or storage, a network transceiver, a display, operating system and application software (e.g., for providing a user interface), and the like. Other components, hardware, and/or software included in the healthcare system 10 that are well known to persons skilled in the art are not shown or discussed herein for brevity.

The consumer devices 14 (referred to collectively as consumer devices 14 and individually as consumer device 14) are used by consumers to interact with the healthcare system 10. Examples of consumer devices 14 include smartphones (e.g., APPLE IPHONE, SAMSUNG GALAXY, NOKIA LUMINA), tablet computers (e.g., APPLE IPAD, SAMSUNG NOTE, AMAZON FIRE, MICROSOFT SURFACE), computers (e.g., APPLE MACBOOK, LENOVO 440), and any other electronic computing device that is capable of accessing information of the cost estimator 12 over the network 18.

The cost estimator 12 may include any number of server computers that operate to estimate costs of healthcare procedures based on healthcare information. The cost estimator 12 may operate to collect a variety of public or provide healthcare data from the healthcare information sources 16. The collected healthcare data is used to estimate the cost of a procedure per healthcare provider and estimate a payout by insurers for a procedure. The healthcare information sources 16 may include any number of servers or other devices that collect, store, generate, and/or provide healthcare-related information to the cost estimator 12 over the network 18.

The healthcare information sources 16 may include any source of healthcare information. For example, the healthcare information sources 16 may include medical facilities, private offices, or devices operated by healthcare professionals. In some embodiments, the healthcare information includes at least portions of claims records, insurer payouts for procedures, or a public fee schedule.

In some embodiments, the cost estimator 12 may provide or administer a portal that allows consumers devices 14 to access a library of information related to healthcare providers and estimated costs for healthcare services. Examples of a portal include a website, mobile application (app), or any channels for providing information about cost-estimation services to the consumer devices 14. As such, the consumer devices 14 can access and filter information about providers, insurers, or cost estimates through the portal of the cost estimator 12.

Figure 2:
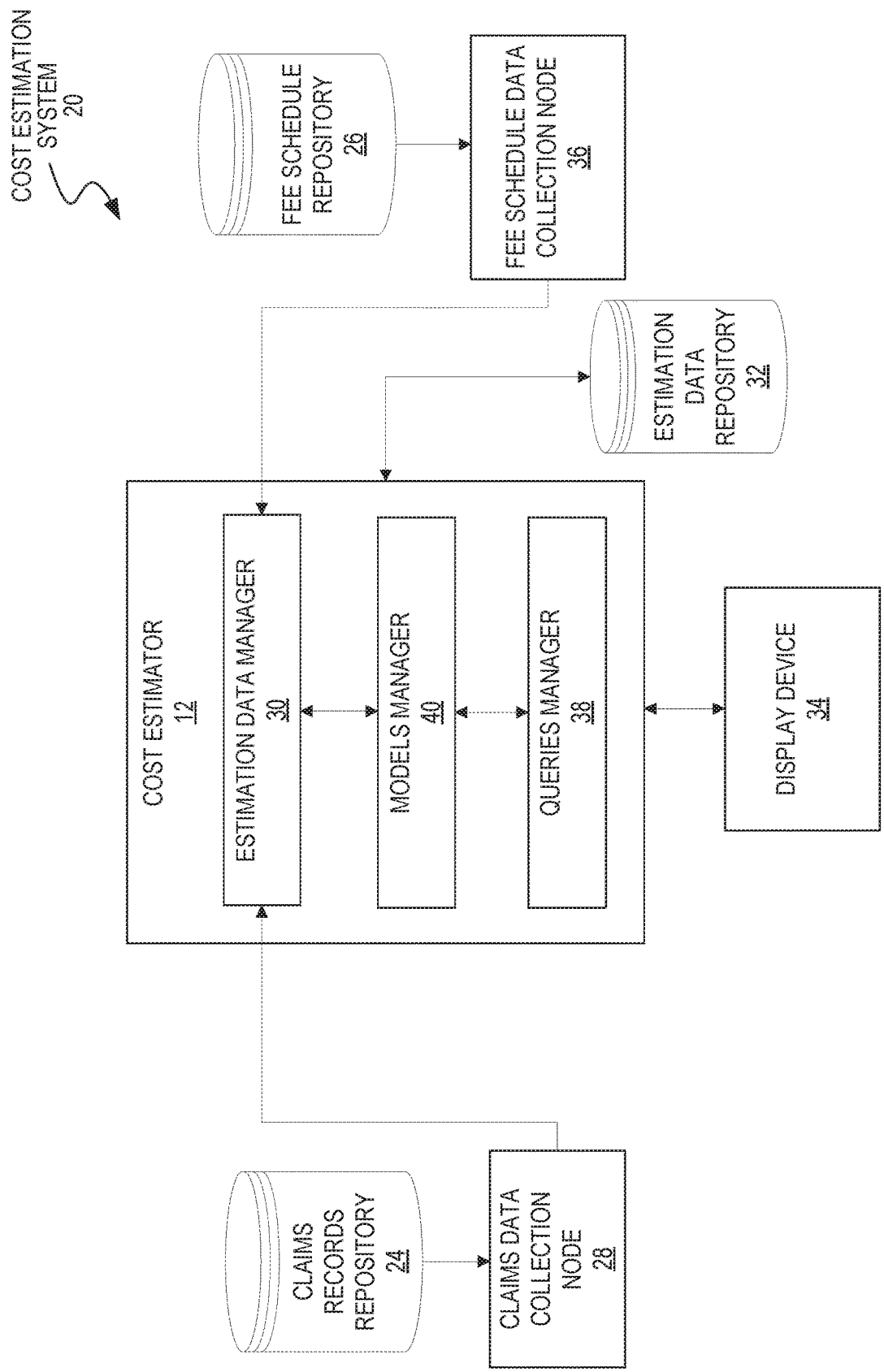
FIG. 2 is a block diagram of a cost estimation system including computing devices in which the described techniques may be implemented according to some embodiments of the present disclosure.

The data processing techniques described herein are suitable for use by systems deployed in a variety of operating environments. FIG. 2 is a block diagram of a cost estimation system 20 of computing devices in which the described technology may be implemented according to some embodiments of the present disclosure. The cost estimator 12 represents server(s) that collect and combine (e.g., correlate) data from both a claims records repository 24 and a fee schedule repository 26.

A claims data collection node 28 obtains claims data from the claims records repository 24. In some embodiments, the claims data collection node 28 can collect claims data by making calls to an application program interface (API) made available by an estimation data manager 30. The claims data collection node 28 may be configured to re-structure or otherwise modify the claims data obtained from the claims records repository 24 to conform to a particular format before being forwarded to the estimation data manager 30 of the cost estimator 12.

The estimation data manager 30 can store the claims data received from claims data collection node 28 in one or more indexes in an estimation data repository 32, which is communicatively coupled to the cost estimator 12. The cost estimator 12 includes instructions for the display of graphical interfaces that may be presented to consumers for obtaining cost estimates of healthcare services. The cost estimator 12 may cause graphical interfaces to display at a display device 34 of a consumer device 14.

A fee schedule data collection node 36 collects fee schedule data from the fee schedule repository 26. In some embodiments, fee schedule data collection node 36 collects fee schedule data by making calls to an API made available by the estimation data manager 30. Accordingly, the claims data collection node 28 and the fee schedule data collection node 36 may forward their data to the estimation data manager 30.

The fee schedule data collection node 36 may be configured to re-structure or otherwise modify the data obtained from the fee schedule repository 26 to conform to a particular format before forwarding the fee schedule data to the estimation data manager 30 at the cost estimator 12. In some embodiments, the estimation data manager 30 can also modify the claims data and fee schedule data to conform to the same format for easier retrieval of both types of data.

The estimation data manager 30 stores the fee schedule data received from the fee schedule repository 26 in one or more indexes in the estimation data repository 32, which is communicatively coupled to the cost estimator 12. The cost estimator 12 also includes instructions for the display of graphical interfaces that may be presented to consumers for estimating costs of healthcare services.

The queries manager 38 of the cost estimator 12 may query the models manager 40 to perform a cost estimate based on an episode of care of a model managed by the models manager 40. Thus, the models manager 40 has access to both collections data and fee schedule data stored in the estimation data repository 32. In an embodiment, software is used to implement functions practiced by any of the computing devices of the cost estimation system 20, including software, which when executed, performs the functionality of any of the computing devices of the cost estimation system 20.

Figure 3:
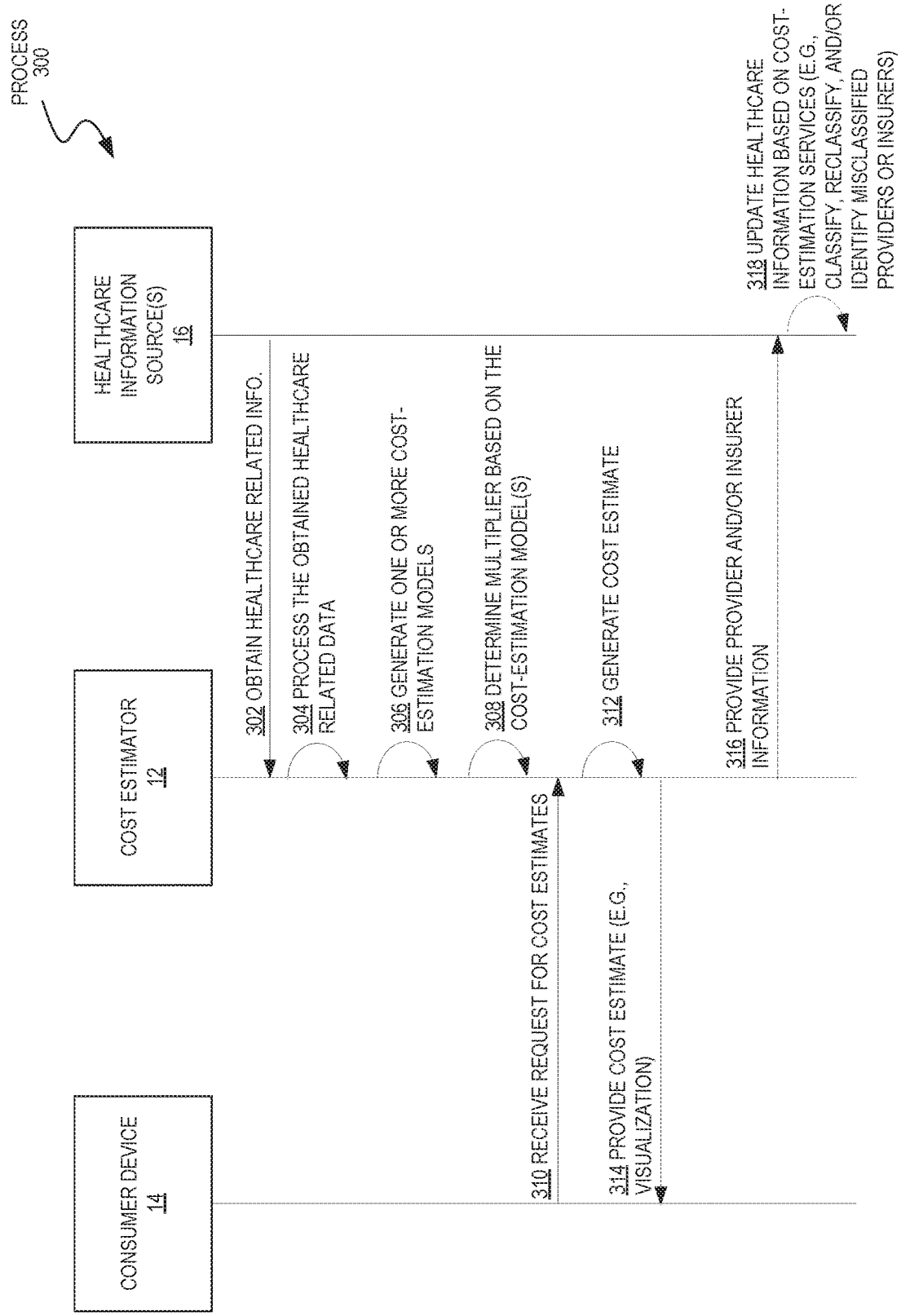
FIG. 3 is a sequence diagram illustrating a process for estimating costs of healthcare services according to some embodiments of the present disclosure.

FIG. 3 is a sequence diagram that illustrates a process 300 for generating a cost estimate for a healthcare service performed by a provider at a facility according to some embodiments of the present disclosure. The cost estimate can be an amount charged to an insurer or an amount paid by the insurer for a given procedure. For example, a user of the consumer device 14 can submit a query to the cost estimator 12 for a cost estimate of a certain procedure. The cost estimator 12 uses information from healthcare information source 16 to generate the cost estimation, and provide it to the user of the consumer device 14.

In step 302, the cost estimator 12 obtain healthcare information from the healthcare information source 16. In some embodiments, the information can be obtained over a network such as the internet. The healthcare information may include content related to healthcare records. For example, the healthcare information may include medical or insurance claim records. A claim record can include data identifying the insurance carrier, the facility where a procedure was performed, and a procedure code. A claim record can also include costs associated with the procedure such as an amount allowed for payment by the insurer, which could be a function of facilities or fee schedules.

In some embodiments, the cost estimator 12 needs only a limited amount of data to estimate costs including data at least indicative of an insurer, healthcare provider, healthcare service, and an amount paid by the insurer to the healthcare provider for the procedure. That is, a minimum amount of data is required to generate accurate costs estimates. For example, the claims records may need data of 200 million or more patients, 900,000 or more doctors, 6.4 billion or more claims, and 24,000 or more facilities. The cost estimator 12 can also obtains a fee schedule used by insurers to determine a payment amount by facility. An example of such a fee schedule is a CMS fee schedule. In some embodiments, at least some of the claim records lack data and the cost-estimator estimates the missing claim data based on other similar data in other similar claims.

The data obtained from the healthcare information sources is not limited to claims data and fee schedules. There could be other sources of information useful for estimating costs. For example, healthcare payment transactions may include a provider identity, provider specialty, practice group, and geographic location (e.g., city and/or state); an insurer, procedure, start-of-claim date. Payment information may also include charges that were paid, reduced, or denied; whether there was a deductible, co-insurance, copay; any bundling or splitting of claims or line items, and methods of payment (e.g., through a clearinghouse). Other relevant data that could be used to estimate costs includes the allowable payment amount by the insurer for a given procedure, diagnosis, or treatment.

In some embodiments, the relationship between private claims data and public fee schedule data may not be readily identifiable. For example, a facility typically negotiates a multiplier that is applied to a public fee schedule. The negotiated multiplier can differ by facility, geographic region, and the like. The multiplier for a facility is applied to the fee schedule to obtain costs for healthcare services. The multipliers used by facilities are usually unknown or unavailable to users such that it is not possible to determine costs for a healthcare service. This deficiency may be intentional to limit competition, or unintentional because a uniform system for cost estimations does not currently exist. To remedy this deficiency, the disclosed technology can estimate the multiplier of a facility to provide accurate cost estimates. Further, any missing information can be extrapolated or estimated from other collected data.

In step 304, data obtained by the cost estimator 12 can be processed for subsequent use to estimate costs. For example, the obtained data may be processed by removing typographical errors, removing outlier data points (e.g., insurer-allowed cost amounts outside a thresholds), and remove any information not used to estimate costs.

In some embodiments, the collected data can be anonymized to protect the privacy of patients or healthcare providers. The identifying information may include, for example, a patient's age, sex, geographic location, procedure date, procedure cost, and any other data that could be used to estimate costs but which could also be used to identify the patient or is indicative of sensitive information about the patient. For instance, claims data may be used to determine the identify of a patient, a physical description of the patient, a condition for which the patient received treatment, the healthcare services provided, and an estimated cost of the treatment.

In some embodiments, the cost estimator 12 can sanitize the collected data by removing data that is unnecessary to estimate costs. The remaining sensitive data can be anonymized to remove data identifying information by using, for example, a cryptographic hash algorithm that accepts claims data and returns hash values. The cryptographic hash algorithm maps any input to a hash value stored and used by the cost estimator 12 to estimate costs. It is deliberately difficult to reconstruct if the input by knowing the stored hash value, which ensures the privacy of the data used for costs estimates.

In some instances, certain cost estimates could vary substantially from the actual costs for a healthcare service, facility, and insurer. For example, the cost estimate for a certain procedure code could deviate substantially even for the same facility or insurer. The deviation could be for the same procedure code on different claims, or for a cost estimate of a procedure code compared to the actual costs. In some instances, certain procedure codes could be consistently difficult to estimate. For example, the procedure codes for surgeries could mask events that add costs to the surgeries.

In step 306, the cost-estimation service generates a model based on the claims data and fee schedule, which could be anonymized. For example, a regression analysis can be applied to the claims data and fee schedule to determine parameters of the linear model. For example, a model can be generated using a Bayesian regression based on the claims data and CMS fee schedule. In some embodiments, the cost estimator 12 can update the mode based on updated or new data received from the healthcare information source 16. For example, the data used to generate a model may be updated periodically (e.g., every 48 hours) with claims data and CMS data that is anonymized before being incorporated into an existing model.

In some embodiments, models are used to identify one or more episodes of care. Since an episode of care for a given healthcare procedure can vary significantly depending on, for example, patient health, doctor specialty and preference, and facility type. The disclosed models are developed to identify episodes of care based on a minimum population to ensure accurate cost estimates. In some embodiments, the models are graphical visualizations that can be rendered on a display device as output and/or for use by an administrator to update the cost estimates by changing the graphical models.

To estimate the cost of a particular procedure, one or more episodes of care are modeled and costs for individual procedures of each episode are calculated. In some embodiments, a model can represent one or more episodes of care. An episode of care may include a target procedure and one or more ancillary procedures. A target procedure refers to a primary procedure for which a consumer sought healthcare services. The target procedure is identified by a procedure code in the claims data. An ancillary procedure is a secondary procedure related to the target procedure, which a patient may undergo in preparation, during, or after undergoing the target procedure. The ancillary procedure may be identified by a procedure code in the claims data. As such, the cost of any episode of care can including the aggregate costs of multiple procedures.

In some embodiments, an ancillary procedure can be defined as any procedure that occurred within a time period from the point at which the target procedure was performed. For example, the time period can be defined as a service window of x days before and after the date at which the target procedure was performed, where x is a predefined non-negative number that limits the scope of what would be considered an ancillary procedure to the target procedure. Examples of ancillary procedures can include diagnostic testing, lab work, anesthesia, etc. The proportion of patients identified in the claims data that received at least one procedure within the service window defining the more episodes of care is computed for each individual service. Whether a representative episode of care includes a service that can also depend on the frequency of such a procedure based on the number of patients undergoing the ancillary procedure in addition to the target procedure.

In some embodiments, an ancillary procedure can be defined as a procedure performed by a provider other than a primary provider. A primary provider may be defined as a provider having a specialty in common with the majority of other providers that performed the targeted procedure. In some embodiments, the primary provider can be the first provider attending to a patient or whose practice is the most specialized of all the providers that attended to a patient. In some embodiments, the provider who performed the most procedures on the patient becomes the primary care provider.

A user seeking to obtain a cost estimate for a procedure can submit a query that is processed with the model to output, for example, an estimate fees to insurers and an estimate of the fees paid by the insurers for the procedure. In other cases, a representative estimate episode of care cost can be computed as a weighted frequency of a combination of individual procedures. As such, the cost estimator 12 can help users choose healthcare services and providers based on potential costs. Examples include aiding users choosing a provider by estimating costs for a procedure performed by a particular doctor and/or having the procedure at a particular facility.

In some embodiments, the cost estimator 12 can determine a frequency for each healthcare procedure across many patients. The cost-estimation service can weigh the cost of each primary healthcare procedures for each secondary healthcare procedure represented in the episode of care across numerous patients by multiplying the frequency associated with each secondary procedure by the cost of the one or more secondary healthcare procedures. The cost estimator 12 can compute a median price for the episode of care by summing each weighted cost of the one or more secondary healthcare procedures for each healthcare procedure represented in the episode of care. The cost estimator 12 can transmit information indicative of a healthcare provider and the estimate cost for the episode of care to the healthcare consumer device 14 for display on its user interface.

In step 308, the cost-estimation service can determine one or more multipliers used to estimate costs based on a combination of a particular insurer, particular provider, and/or procedure code. Specifically, a healthcare system includes various providers (e.g., doctors, facilities) that submit claims for services to various insurers. The claims can include different amounts of fees charged for the same or similar procedures. The claims can also indicate what amount of the charged fees were paid to the providers.

In the case of certain fee schedules such as a CMS schedule, a multiplier is applied to scale the fees for a geographic location, healthcare provider, insurer, or the like. Accordingly, a multiplier can have different values for different locations, providers, or insurers. For example, there could exist a multiplier value for a particular insurance program (e.g., Medicare) used to set fees for a particular facility by a particular insurer. As such, the cost is a function of a topic, facility, and insurer estimated by the sum of the price multiplied by the frequency for a particular procedure code. For example, the cost can be expressed mathematically as:

$$\text{Cost (topic, facility insurer)} = \sum_{proc\_code} \text{price}(proc_{code}) \times \text{frequemcy}(proc_{code})$$

As shown, the topic can include a procedure. The facility is a type of provider such as a hospital or clinic. The insurer is an insurance carrier. The "proc_code" refers to the procedure code of the procedure. Thus, the cost is a function of the topic, facility, and insurer, which equals the sum of the price multiplied by frequency for each per procedure code for an episode of care. In this embodiment, the price is an example of the unknown multiplier.

In some embodiments, a linear model for an episode of care can be expressed per facility and insurer as price (insurer, facility, code)=slope×price$_{Medicare}$+intercept+stochastic error. The slope of this linear model is a multiplier applied to a local Medicare price used to set prices for the facility and insurer. A number of models can be fit across combinations of facilities and insurers to obtain a robust matrix used to estimate multiplier values per facility and insurer and across multiple facilities and insurers. For example, a matrix may include:

$$\text{Insurers} \begin{pmatrix} M_{1,1} & M_{1,2} & M_{1,3} \\ M_{2,1} & M_{2,2} & M_{2,3} \\ M_{3,1} & M_{3,2} & M_{3,3} \end{pmatrix} \overset{\text{Facilities}}{}$$

As shown, the matrix includes multiplier values M1 through M9 for each combination of insurer $I_1$ through $I_3$ and facility $F_1$ through $F_3$. The matrix can be used to estimate how much a particular insurer would pay for a particular procedure performed at a particular facility. For example, if a Medicare payment of Z is made to insurer Ix for a procedure performed at $F_y$, then $I_x$ will pay $Z*M_{x,y}$. For example, if Z=$100 and $M_1$=2.9, then $I_x$ will pay $290 for the procedure.

The multiplier can be used to perform a variety of cost estimate analytics. For example, multiplier values can be used to estimate costs as a function of a geographic location (e.g., city, state, region). The multiplier can vary significantly by location. As a result, for example, costs for services performed in certain locations of California can be greater compared to locations in Kentucky. However, the multiplier values can also be different between insurers in the same locations.

In another example, multiplier values can be compared to market shares per for geographic locations to determine any correlations. In another example, the multiplier values can be used to rank insurers for a particular facility. As such, the multiplier values can be used to estimate cost per facility or insurer. The results could then be compared to, for example, market share to obtain insights about how multipliers affect market share at particular locations. In some embodiments, a cost estimation algorithm can scale to deal with existing and emerging challenges.

The multiplier data or data derived from the multiplier data can be stored in memory for later use to estimate costs. For example, the multiplier data can be indexed for use in reconstructing a cost estimation matrix or to reconstruct an EPISODE OF CARE model for use when estimating costs.

In step 310, the cost estimator 12 receives a request from the consumer device 14 for a cost estimate. For example, the cost estimator 12 may administer or control a portal accessible by a user through the consumer device 14. The portal may be an app or website displayed on a display screen of the consumer device 14. The portal allows the user of the consumer device 14 to define parameters such as a procedure, provider, insurer, location, or any other data that could affect the cost estimate. The request may be for a comparison of cost estimates or for a particular cost estimate. For example, a user can request a cost comparison for a procedure performed by different providers in a specified location.

In some embodiments, the parameters of the request may define how results are presented to the user. For example, the user of the consumer device 14 may request a ranking of providers that have performed the greatest number of the same type of procedure in a particular geographic location relative to other providers.

In some embodiments, the user of the consumer device 14 may obtain search parameters from a source other than user input. For example, a user's current geographic location could be determined from Global Positioning System (GPS) coordinates of the consumer device 14. The portal used for searching cost estimates may automatically populate a location field with the location of the consumer device 14. In another example, the portal could automatically populate other search parameters retrieved from other sources of the consumer device 14 or information obtained by the user when registering to use the search portal. As such, a user of the consumer device 14 can request assistance from the cost estimator 12 in choosing a provider to perform a specific procedure, which could be narrowed by a specific insurer or a certain geographic location.

In some embodiments, a search portal can be displayed on user interface (UI) for a user to search cost estimate information. For example, a UI can include a search field that can receive queries from a user. The query can include a command to search for basing a cost estimate on a particular codebook. A query may include a command to base a cost estimate on a Medicare fee schedule.

In some embodiments, the data can be presented in a user friendly manner to help provide meaningful insights to the user. For example, FIG. X is a map of the United States showing a state-wise and facility type slope coverage based on the cost estimates analysis. In this example, each states the proportion of all insurers that have a certain claim given any eligible facility. As shown, the proportion of hospitals and clinics with any eligible facilities that have a certain claim are 0.16 and 0.24, respectively. In other embodiments, the collected or estimated data can be presented in an state-wise manner without scaling. For example, the raw data can be presented as for eligible facility and insurer with respect to the same procedure code.

In step 312, the cost estimator 12 estimates a cost that satisfies the parameters of the given request. The cost estimator 12 can use the given parameters to identify an episode of care model to estimate a cost including the target procedure. For example, the cost estimator 12 can estimate the cost of an episode of care including a target procedure and predicted ancillary procedures performed by particular providers at particular facilities for a particular insurer. In particular, the cost estimator 12 can identify a suitable multiplier value based on the request. For example, user-defined insurer and facility parameters can be used to identify a matching multiplier value of the aforementioned cost estimation matrix.

In some embodiments, an episode of care is identified automatically by using a graph traversal model or an algorithm to detect any episode of care and evaluate its validity. For example, the detection of an episode of care can involve calculating probabilities for each type of episode of care sequence, an interpretation of the model including relative-expense of a facility-insurance combination, and result in ranking facilities by cost. Estimating code costs can involve performance analysis, and an analysis of outliers including coding practice nuances and incorrect codes (e.g., mistakes or fraud).

An episode of care model can be selected from among multiple models. In some instances, the choice of the selected model is key to obtaining accurate estimate costs, as well as accounting for missing data. This can be achieved by using a standard data set (e.g., CMS) as a reference to greatly simplify the model, and data that does not fit the model can reveal interesting insights.

In some embodiments, the cost estimator 12 can establish an estimated cost of procedures of an episode of care based on one or more aggregation levels, from most geographically specific to least geographically specific. The cost estimator 12 can establish this estimated price of all procedures in an episode of care for a particular insurer or across all insurers. In one embodiment, the cost estimator 12 can use multiple levels of aggregation including a median price for each combination of provider and insurer, a median price for each combination of practice group and insurer, a median price for each combination of insurer and city, a median price for each combination of insurer and state, and a median price for each combination of insurer on a nationwide basis.

In some embodiments, the process for estimating costs involves applying weights to the claims and payment information used to build the models. The weights may be adjusted based on machine learning techniques that improve the accuracy of the weights over time. For example, a training dataset of claims data or payment data can be input into a machine learning algorithm. Claims or payment data with missing data can be input into the machine learning algorithm to render estimates for the missing data. An expert can verify whether the estimates are correct to assist the machine learning in making future estimates. After some initial training period, the machine learning algorithm may yield estimates with sufficient accuracy such that it could be applied to reliably estimate the missing data. The machine learning algorithm could continue to iteratively refine or adjust the value of weights applied during the cost-estimation process over time.

In one embodiment, the weights may require manual adjustments in order to account for bias in payment information and other inherent noise/bias. For these weights to be adjusted, each procedure in an episode of care may be manually curated or predefined into distinct groups or buckets. Each bucket contains a set of service codes which denote the set of ancillary or related procedures a patient usually receives when a patient receives a primary service. For instance, patients generally receive anesthesia when receiving a colonoscopy. The frequencies of each service are conditioned on receiving at least one service in the bucket. For example, among all patients who received an IUD insertion procedure, only 80% of episodes may include a code for the specific brand of IUD. An assumption is made that every IUD insertion procedure code must have an associated code designating the IUD brand, so the associated code for the IUD brand is weighted in a bucket separate from the insertion code. Separating the IUD brand and the insertion code in this way adjusts the weight of the IUD brand to 100%.

In one embodiment, the procedures that are manually curated and grouped into buckets may undergo an administratively controlled review process for quality assurance to ensure that the grouping logic is sound and that the estimated price is representative of a typical episode of care that a patient might experience. Sometimes this review process may involve an external medical coding expert. This process serves a secondary purpose: ensuring the appropriateness of an episode of care across all providers, so that fair comparisons can be made by the user.

To produce a price for an episode of care for a target service for a specific provider, we sum across the expected costs of each individual procedure included in the episode of care. Each procedure's expected cost is calculated by multiplying the unweighted procedure's price by the expected frequency for a patient to receive that service. To calculate the expected frequency, the provider proportion must be weighted by the number of patients they treated. This process of weighting is repeated for every provider in the database.

In step 314, the cost estimator 12 responds to the request from step 310 by providing one or more estimate costs that satisfy the parameters of the request. For example, multiple estimate costs that satisfy the procedure, facility, and insurer parameters of search query can be provided for display on the consumer device 14 as a list of matching providers and respective estimated costs. For example, the cost estimator 12 may return provider information to a website or software application resident on the consumer device 14. The list of matching providers may be ranked by the strongest match to the indicated procedure and insurer and/or information comparing the matching providers, or the "average" provider providing the indicated procedure. In some embodiments, a profile of a particular provider can be requested via the consumer devices 14. The profile may be based on estimating procedure costs and can provide insights into healthcare insurer payouts for a given procedure, such as the net cost for a patient undergoing a target procedure with that particular provider.

In some embodiment, the cost estimator 12 provides a cost exploration tool for the consumer device 14. The cost exploration tool can provide insights into the costs of procedures per provider in a particular geographic area. For example, in response to searching for procedure costs for a particular doctor practicing in a particular zip code, the tool can provide information about the cost of a given procedure for that doctor nearest the user. In another embodiment, the technology can also provide insights into the relationship between quality of care and cost of care. For example, in response to searching for procedure costs for a particular doctor, the disclosed technology can provide information about a comparable doctor that charges less for the same procedure.

In step 316, the cost estimator 12 may optionally provide information about the identified healthcare provider or insurer to the healthcare information sources 16. For example, the information can include how to properly classify healthcare providers based on the procedures most often rendered or the insurance most often accepted. Lastly, in step 318, the healthcare information sources 16 can optionally update healthcare information to reflect newly determined information about the identified healthcare providers. As such, the healthcare information sources 16 can classify, identify misclassified, and/or reclassify healthcare providers in accordance with their cost-estimation services.

Figure 4A:
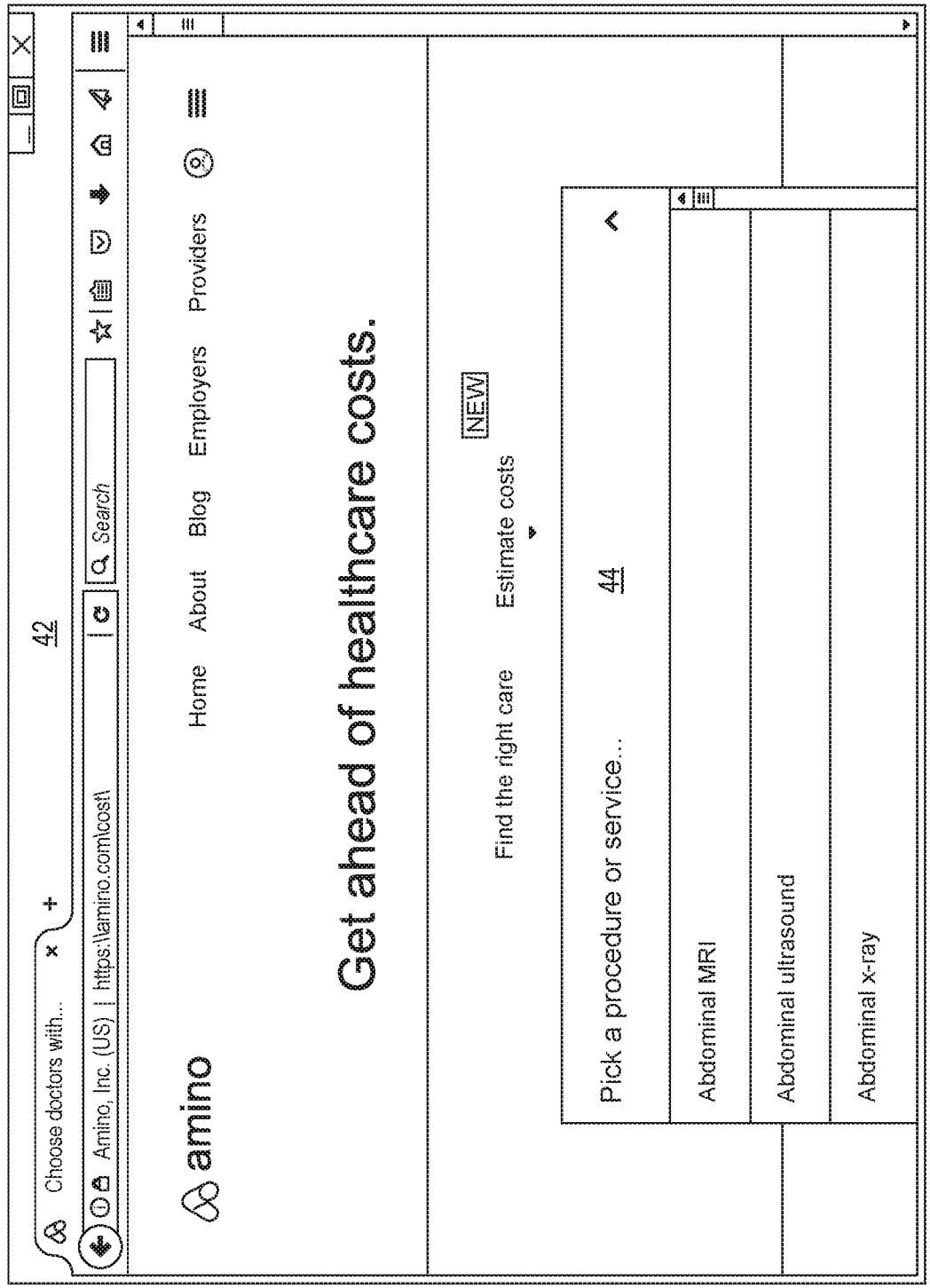
FIG. 4A illustrates a graphical interface used to query estimate costs of healthcare services according to some embodiments of the present disclosure.

FIG. 4A illustrates a graphical interface used to query for estimate costs of services according to some embodiments of the present disclosure. The web browser 42 is rendering a graphical interface. The graphical interface includes a text box 44 that can receive user input defining a procedure or service. As shown, a dropdown list includes a selectable procedures or services. Upon receiving an input, one or more other displays can be rendered by the web browser 42.

Figure 4B:
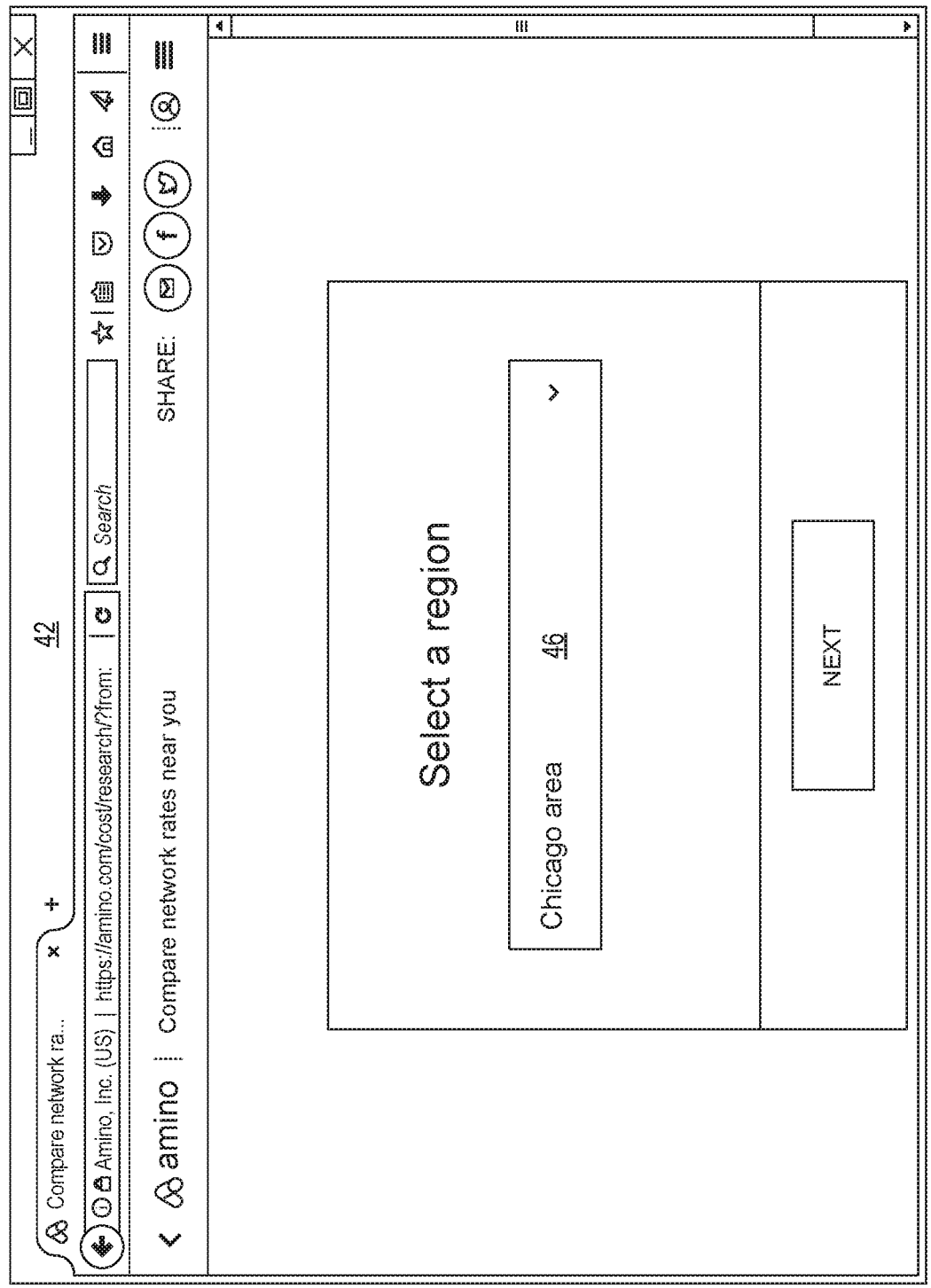
FIG. 4B illustrates a graphical interface used to constrain estimate costs of healthcare services to a particular geographic region according to some embodiments of the present disclosure.
Figure 4C:
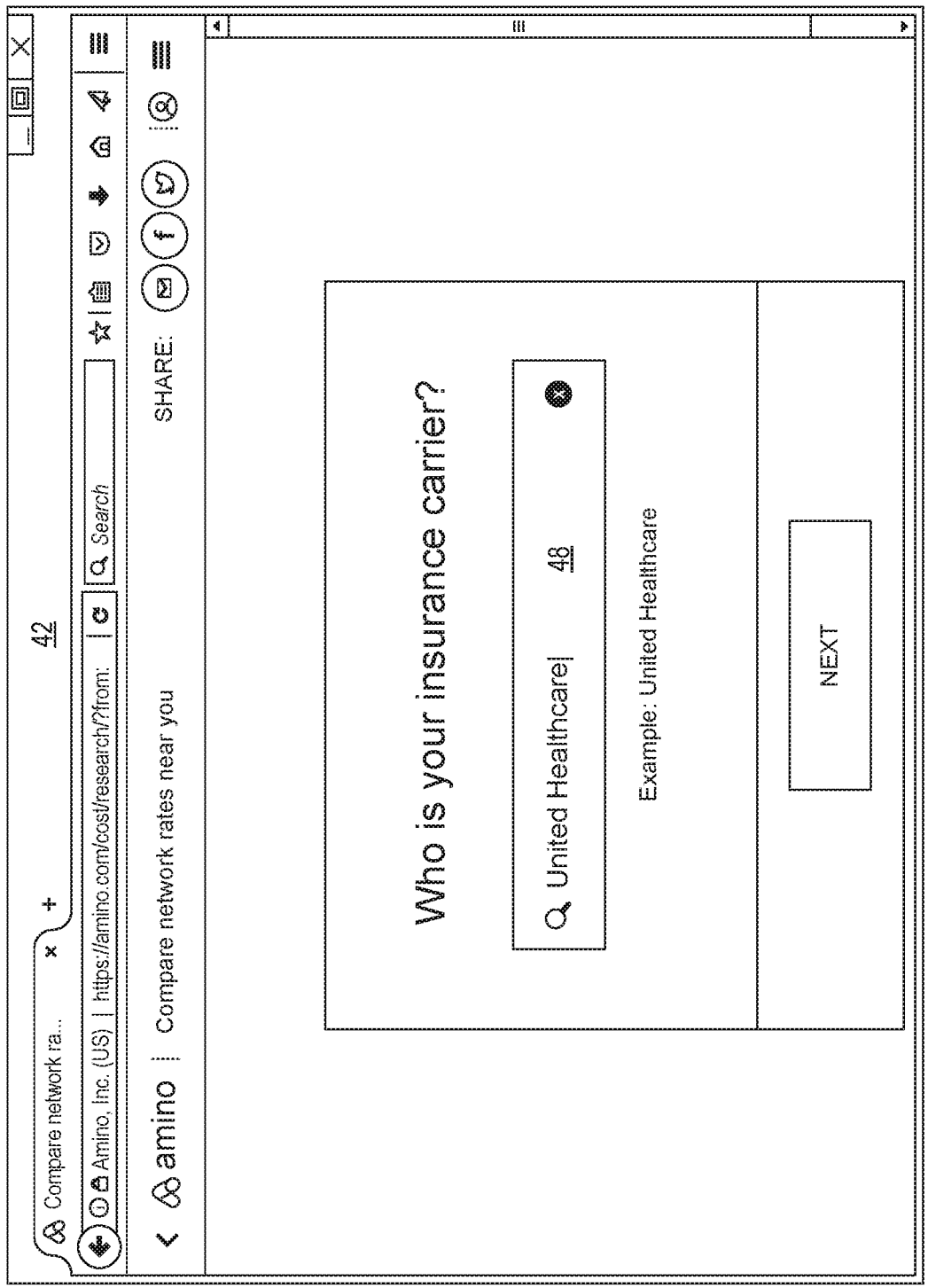
FIG. 4C illustrates a graphical interface used to constrain estimate costs of healthcare services to an insurer according to some embodiments of the present disclosure.

The displays may prompt users to input constraints used to accurately estimate costs. The constraints may include a geographic region, insurer, and the like. For example, FIG. 4B illustrates a graphical interface used to constrain a query for estimate costs of services to a particular geographical region. As shown, a selected geographic region can be input by a user into the text box 46. FIG. 4C illustrates a graphical interface used to further constrain the query for estimate costs of services to a particular insurance carrier that can be input by a user into the text box 48.

Figure 4D:
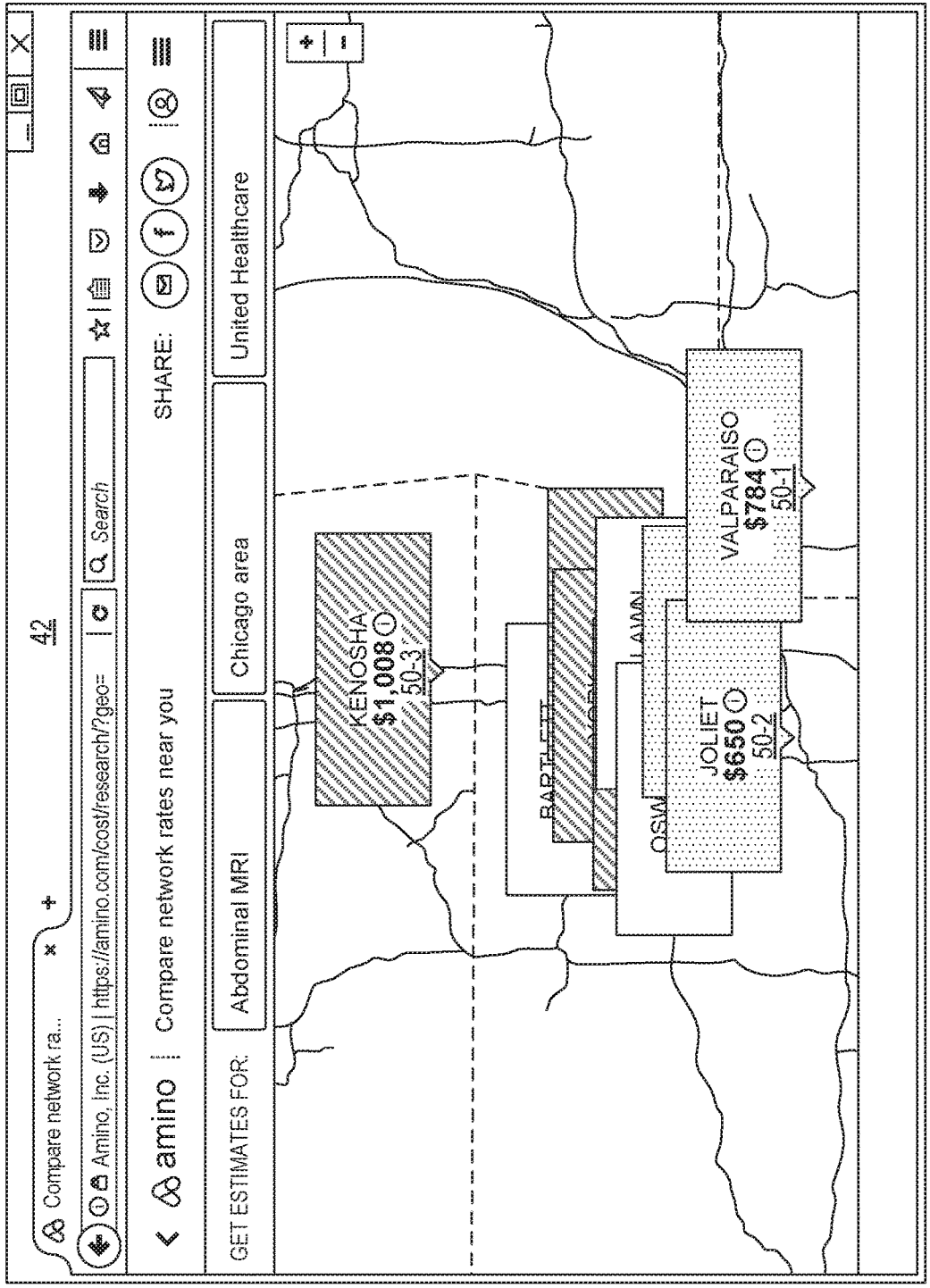
FIG. 4D illustrates a graphical interface showing estimate costs for the same healthcare service constrained by a geographic region and insurer according to some embodiments of the present disclosure.

After the selected procedure or service and constraints have been input, the cost estimation services can generate a display including cost estimates. For example, FIG. 4D illustrates a graphical interface showing estimate costs a particular service within a particular region covered by a particular insurance carrier. As shown, insurer specific boxes 50 are displayed to overlay a map of a selected geographic region. Each of the boxes 50 can be colored to readily indicate whether cost estimates of a particular box 50 is low, typical, or high for the geographic region. Any of the cost estimate boxes 50 can be selected to reveal detailed cost estimate data for a particular insurer in a particular geographic region.

Figure 4E:
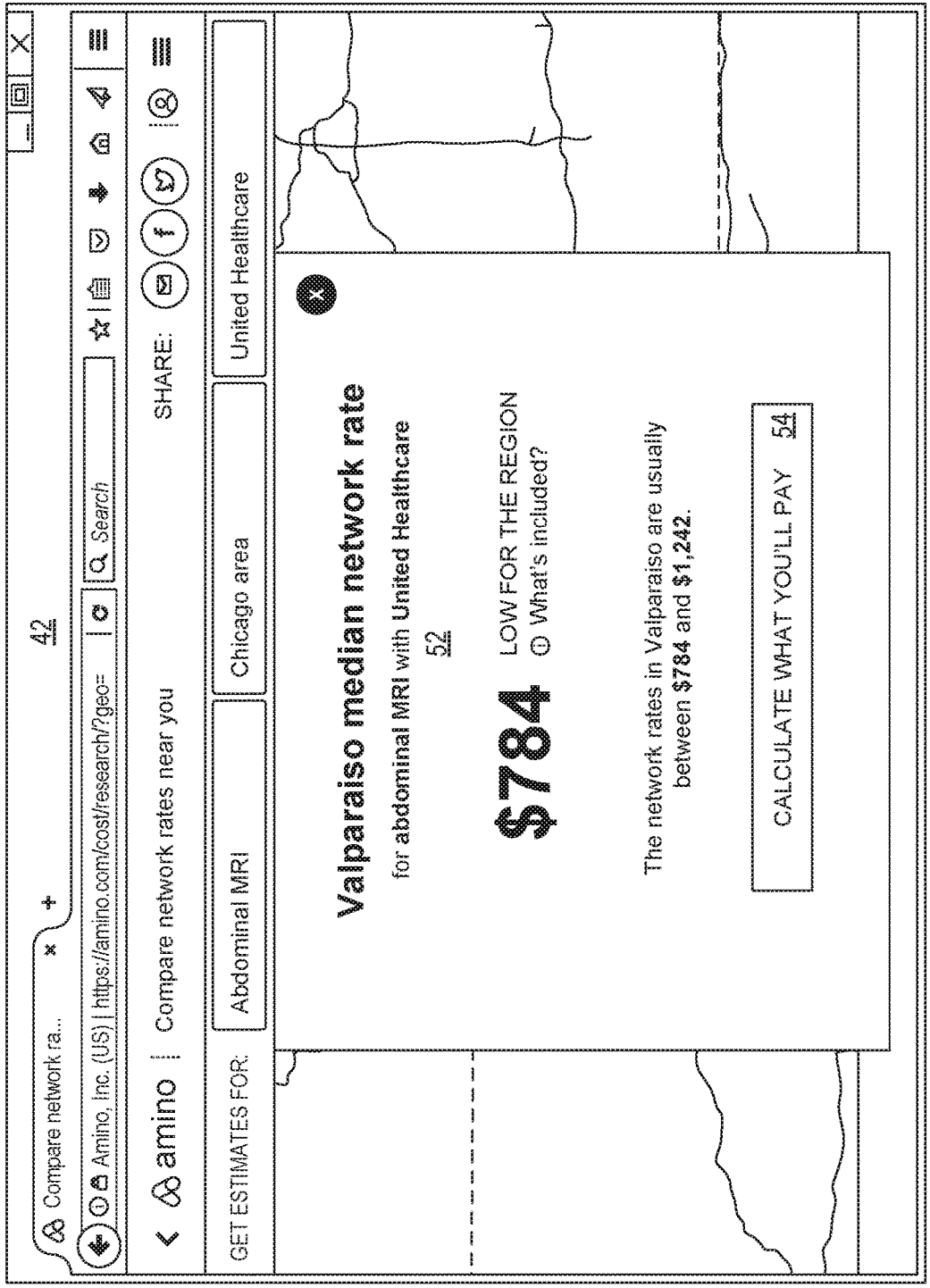
FIG. 4E illustrates a graphical interface showing information of a selected network rate according to some embodiments of the present disclosure.

For example, FIG. 4E illustrates a graphical interface showing data for a particular insurer in the particular geographic region. The display of FIG. 54 can be generated in response to selected the estimate box 50-1. As shown, a window 52 includes the Valparaiso median network rate for an abdominal MRI with United healthcare estimated at $784. The user can also click an option 54 to calculate what the user is estimated to need to pay for this medical service.

Figure 4F:
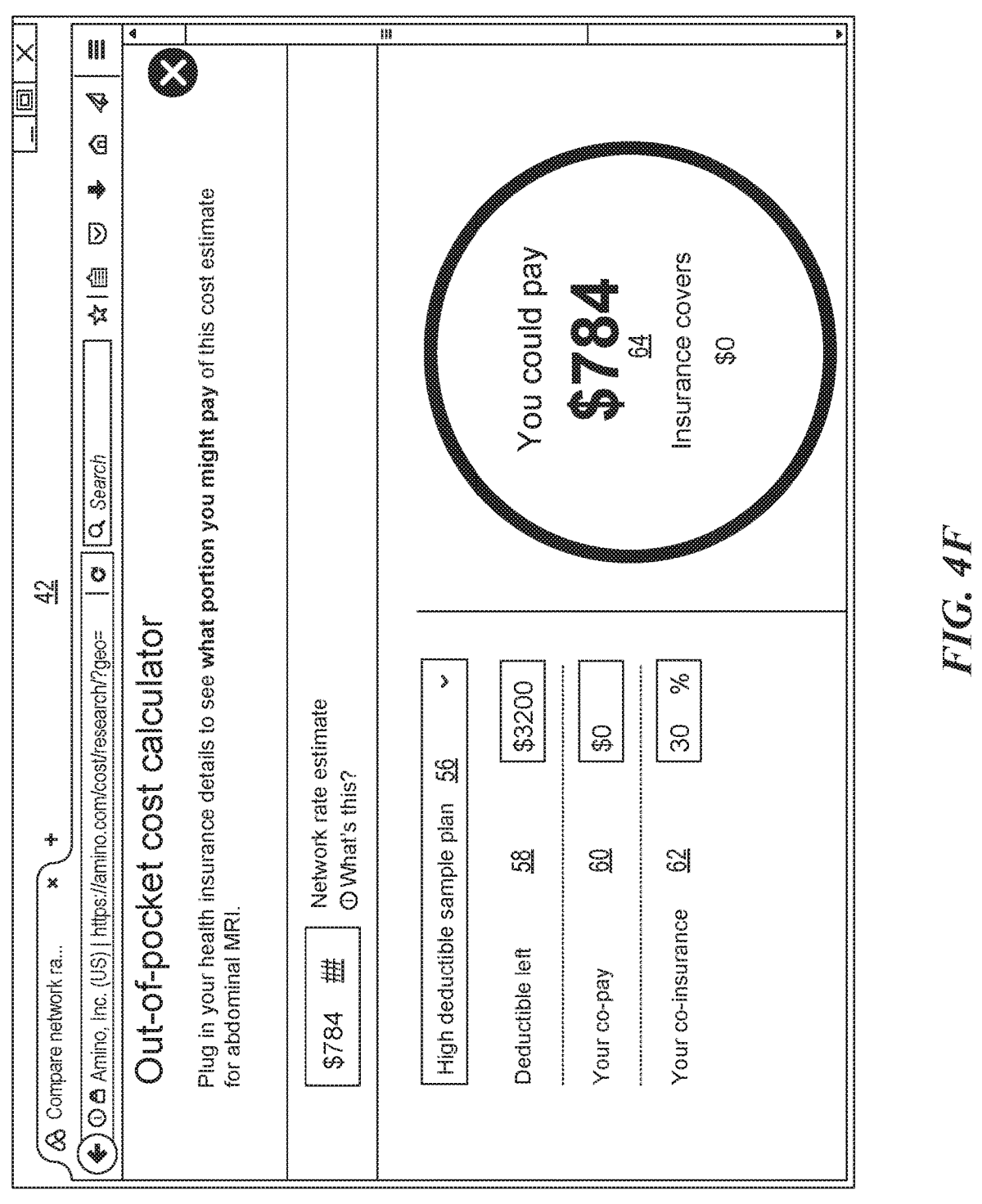

For example, FIG. 4F illustrates a graphical interface showing data for a personalized calculation of costs estimates. The web browser 42 renders a window including customizable features for personalizing the network rate estimate for the particular user. As shown, these features include a plan type 56, deductible left 58, co-pay amount 60, and percentage covered by a co-insurance 62. The calculated personal costs estimates are rendered in a visualization 784 after the user has customized the aforementioned options.

Figure 5:
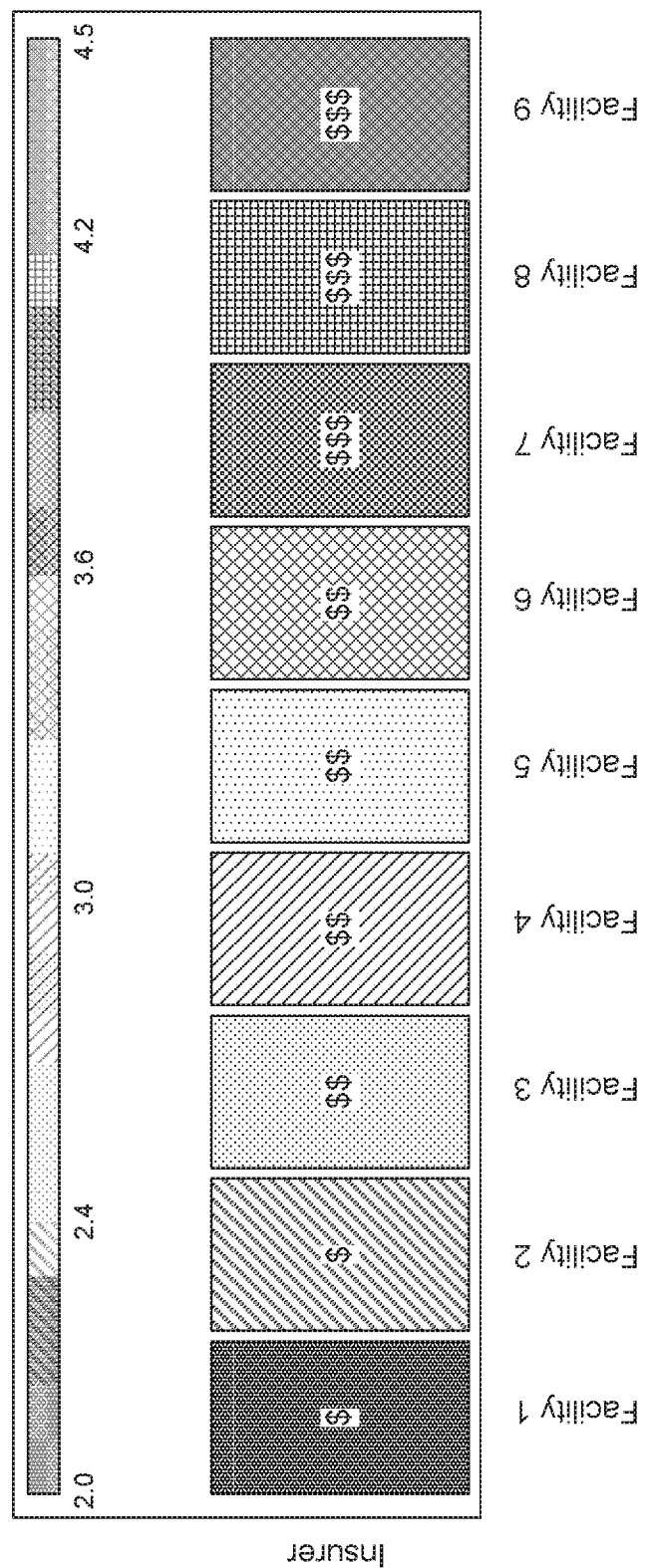
FIG. 5 illustrates a visualization of costs estimates for a healthcare service according to some embodiments of the present disclosure.

The cost estimates can be scaled or sorted to provide additional useful insights that could aid a user in choosing a facility for a procedure. For example, FIG. 5 illustrates a visualization of costs estimates for a procedure according to some embodiments of the present disclosure. In particular, FIG. 5 is a scale that illustrates the relative estimate cost charged by an insurer for a procedure performed at facilities 1 through 9. The relative estimate costs are scaled to range between 2.0 and 4.5, where 3.5 is the average estimate cost. The scaled range is also depicted by different shades and a number of "$," where fewer "$" indicate the estimate cost is relatively less expensive and more "$$" indicate that the estimate cost is relatively more expensive. For example, Facility 5 has a relatively lighter shade compared to Facility 9. Further, Facility 5 is labeled "$$" and Facility 9 is labeled $$$. Thus, Facility 5 is less expensive than Facility 9.

The displayed estimated costs can be further arranged, sorted, filtered, or otherwise processed to provide meaningful information to users seeking relevant cost estimate information. The scope of the estimated costs can depend on the procedure codes included in the claims. In some instances, some or all procedure codes of a fee schedule could be estimated. For example, cost estimates can be determined for each and every procedure code listed in a CMS fee schedule. The cost estimates may be sorted by facility type and insurer. For example, the costs estimates can be sorted by hospital or client and/or by insurer such as per hospital or clinic and its top insurer, or per hospital or client and any eligible insurance.

The disclosed embodiments can include various use cases. For example, multiplier dispersion can be based on facility type in cities. An extension is also to look at place of service type based on revenue code. For example, a difference in multiplier between emergency centers and urgent care units. In another use case, the multiplier can be used to determine why insurers in comparison to each other paying higher or lower. For example, it can be determined whether this is because of value added services. In yet another use case, the data can be used to determine a relationship between difference in multipliers of insurance companies and new market share that insurers want to grab in the upcoming year.

Figure 6:
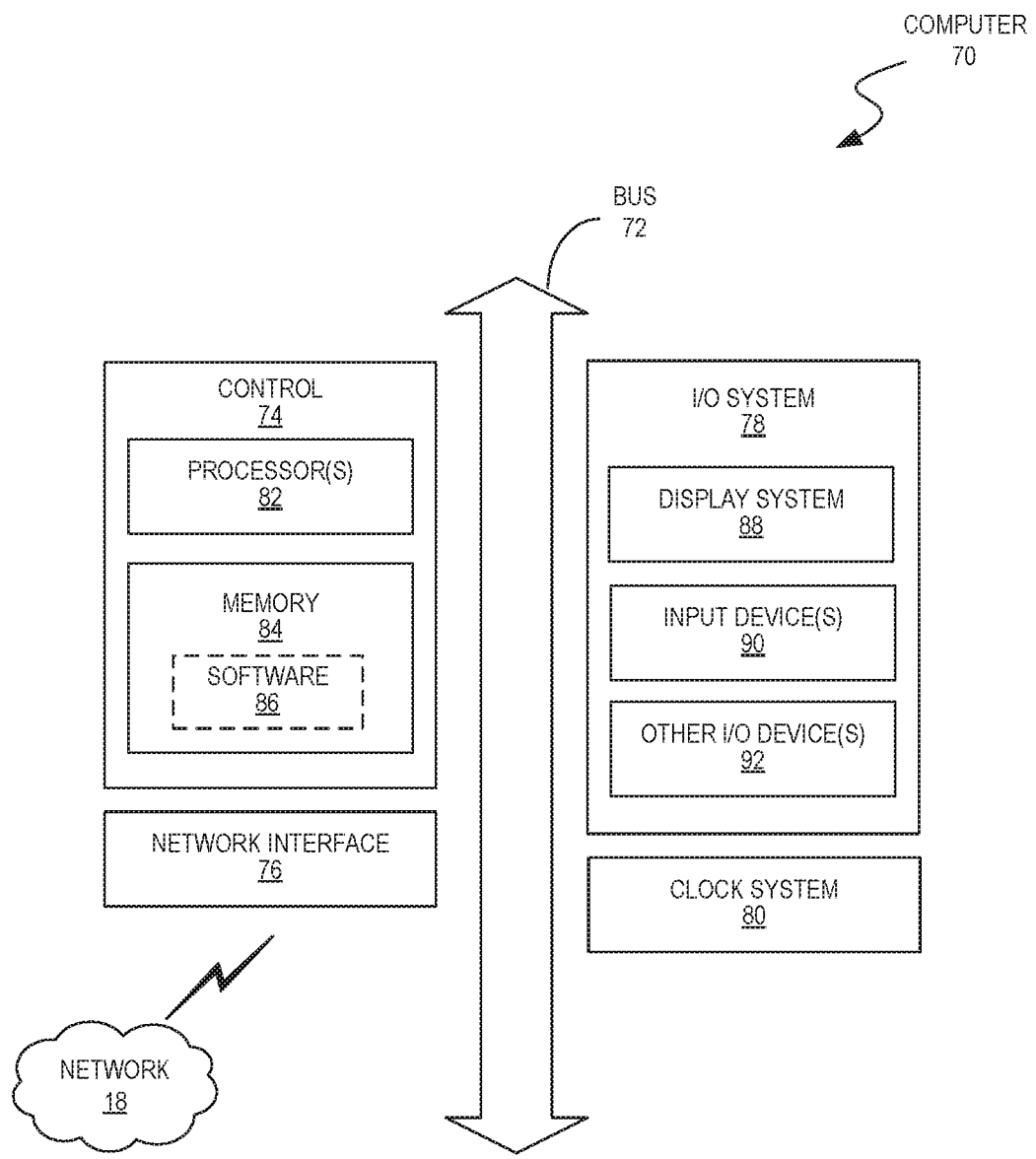
FIG. 6 is a block diagram illustrating a computer operable to implement the disclosed technology according to some embodiments of the present disclosure.

FIG. 6 is a block diagram of a computer 70 operable to implement the disclosed technology according to some embodiments of the present disclosure. The computer 70 may be a generic computer or specifically designed to carry out features of healthcare system 10. For example, the computer 70 may be a system-on-chip (SOC), a single-board computer (SBC) system, a desktop or laptop computer, a kiosk, a mainframe, a mesh of computer systems, a handheld mobile device, or combinations thereof.

The computer 70 may be a standalone device or part of a distributed system that spans multiple networks, locations, machines, or combinations thereof. In some embodiments, the computer 70 operates as a server computer (e.g., the cost estimator 12 or healthcare information sources 16) or a client device (e.g., consumer devices 14) in a client-server network environment, or as a peer machine in a peer-to-peer system. In some embodiments, the computer 70 may perform one or more steps of the disclosed embodiments in real time, near real time, offline, by batch processing, or combinations thereof.

As shown in FIG. 6, the computer 70 includes a bus 72 that is operable to transfer data between hardware components. These components include a control 74 (e.g., processing system), a network interface 76, an input/output (I/O) system 78, and a clock system 80. The computer 70 may include other components that are not shown nor further discussed for the sake of brevity. One having ordinary skill in the art will understand any hardware and software that is included but not shown in FIG. 6.

The control 74 includes one or more processors 82 (e.g., central processing units (CPUs)), application-specific integrated circuits (ASICs), and/or field-programmable gate arrays (FPGAs), and memory 84 (which may include software 86). For example, the memory 84 may include volatile memory, such as random-access memory (RAM), and/or non-volatile memory, such as read-only memory (ROM). The memory 84 can be local, remote, or distributed.

A software program (e.g., software 86), when referred to as "implemented in a computer-readable storage medium," includes computer-readable instructions stored in the memory (e.g., memory 84). A processor (e.g., processor 82) is "configured to execute a software program" when at least one value associated with the software program is stored in a register that is readable by the processor. In some embodiments, routines executed to implement the disclosed embodiments may be implemented as part of an operating system (OS) software (e.g., Microsoft Windows® and Linux®) or a specific software application, component, program, object, module, or sequence of instructions referred to as "computer programs."

As such, the computer programs typically comprise one or more instructions set at various times in various memory devices of a computer (e.g., computer 70), which, when read and executed by at least one processor (e.g., processor 82), will cause the computer to perform operations to execute features involving the various aspects of the disclosed embodiments. In some embodiments, a carrier containing the aforementioned computer program product is provided. The carrier is one of an electronic signal, an optical signal, a radio signal, or a non-transitory computer-readable storage medium (e.g., memory 84).

The network interface 76 may include a modem or other interfaces (not shown) for coupling the computer 70 to other computers over the network 18. The I/O system 78 may operate to control various I/O devices, including peripheral devices, such as a display system 88 (e.g., a monitor or touch-sensitive display) and one or more input devices 90 (e.g., a keyboard and/or pointing device). Other I/O devices 92 may include, for example, a disk drive, printer, scanner, or the like. Lastly, the clock system 90 controls a timer for use by the disclosed embodiments.

Operation of a memory device (e.g., memory 84), such as a change in state from a binary one (1) to a binary zero (0) (or vice versa) may comprise a visually perceptible physical change or transformation. The transformation may comprise a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

While embodiments have been described in the context of fully functioning computers, those skilled in the art will appreciate that the various embodiments are capable of being distributed as a program product in a variety of forms and that the disclosure applies equally, regardless of the particular type of machine or computer-readable media used to actually effect the embodiments.

While the disclosure has been described in terms of several embodiments, those skilled in the art will recognize that the disclosure is not limited to the embodiments described herein and can be practiced with modifications and alterations within the spirit and scope of the invention. Those skilled in the art will also recognize improvements to the embodiments of the present disclosure. All such improvements are considered within the scope of the concepts disclosed herein. Thus, the description is to be regarded as illustrative instead of limiting.

From the foregoing, it will be appreciated that specific embodiments of the invention have been described herein for purposes of illustration, but that various modifications may be made without deviating from the scope of the invention. Accordingly, the invention is not limited except as by the appended claims.

The invention claimed is:

1. A method performed by one or more server computers to generate models of location based data for machine learning analysis, the method comprising:
   obtaining, by a server, a plurality of healthcare claim data records corresponding to a plurality of healthcare facilities, each of the plurality of records having fields, the fields including:
      a location;
      a doctor;
      a procedure code; and
      an episode;
   generating, by the server, a model based on training data including the plurality of records that predicts a likelihood for a given value in the doctor and the procedure code fields based on known values in the episode and location fields;
   determining, by the server, a multiplier for each of the plurality of healthcare facilities based on the model, wherein a first multiplier associated with a first healthcare facility is indicative of a value used to scale a public healthcare fee schedule to a first procedure code associated with a first episode at the first healthcare facility performed by a first doctor;
   receiving, by the server, user input specifying the episode and a region containing multiple values for the location field; and
   determining, based on the user input and the model, corresponding procedure codes, corresponding doctors, and corresponding locations.

2. A method performed by one or more server computers, the method comprising:
   obtaining private healthcare insurance claims data and public healthcare fee schedule data from one or more data sources;
   generating a model based on training data including a combination of the private healthcare insurance claims data and the public healthcare fee schedule data; and
   determining a multiplier for each of the plurality of healthcare facilities based on the model, wherein a first multiplier associated with a first healthcare facility is indicative of a value used to scale the public healthcare fee schedule for the first healthcare facility such that a cost for a healthcare service associated with the first healthcare facility is estimated based on the first multiplier of the healthcare facility.

3. The method of claim 2, wherein the public healthcare fee schedule data is Centers for Medicare & Medicaid Services data.

4. The method of claim 2, further comprising, prior to generating the model:
   removing data identifying any patients from the private healthcare insurance claims data and the public healthcare fee schedule data.

5. The method of claim 2, further comprising:
   receiving a query to estimate a cost of a particular healthcare service performed at a particular healthcare facility;
   calculating a particular cost estimate for the particular healthcare service based on a particular multiplier value associated with the particular healthcare facility; and
   causing display of the cost estimate or data indicative of the cost estimate for the particular healthcare service.

6. The method of claim 5, wherein the model defines a plurality of episodes of care, each having a frequency weighted combination of the particular healthcare service and at least one additional healthcare service, and the particular of cost estimate is based on a normalized aggregate of costs for the services including in the plurality of episodes of care.

7. The method of claim 5, further comprising, prior to calculating the particular cost estimate:
   receiving user input indicating a geographic region, wherein the query for the particular cost estimate is constrained by the geographic region such that the particular cost estimate is constrained to the geographic region.

8. The method of claim 5, further comprising, prior to calculating the particular cost estimate:
   receiving user input indicating a particular insurer, wherein the query for the cost estimate is constrained by the insurer such that the particular cost estimate is constrained to the insurer.

9. The method of claim 2, wherein generating the model comprises:
   ascertaining, from the private healthcare insurance claims data and the public healthcare fee schedule data, a plurality of data points each having healthcare facility and insurer pair; and
   performing a Bayesian regression on the data points to generate the model as a linear model where the slope of the linear model represents a multiplier.

10. The method of claim 9, further comprising:
    obtaining additional data points;
    performing a Bayesian regression including the additional data point to generate an updated model for an updated linear model.

11. The method of claim 2, further comprising:
    generating a plurality of additional models including a model that accounts for healthcare providers, a model that accounts for patient histories, a model that accounts for comorbidities, and a model that accounts for secondary healthcare providers.

12. The method of claim 2, further comprising:
updating the model based on machine learning techniques.

13. The method of claim 2, wherein the model facilitates any of discovering of re-negotiated costs by an insurer, projecting estimates of missing data in the private healthcare insurance claims data based on historical data, or identifying outlier data points of the model indicative of errors, fraudulent claims, negotiated cost patterns, or cost policies.

14. The method of claim 2, further comprising:
receiving a query to estimate a cost of a particular healthcare service performed at a particular healthcare facility;
calculating a particular cost estimate for the particular healthcare service based on a particular multiplier value associated with the particular healthcare facility; and
causing display of a visualization indicative of the particular cost estimate.

15. The method of claim 2, further comprising:
receiving a query to estimate a cost of a particular healthcare service performed at a particular healthcare facility;
calculating a particular cost estimate for the particular healthcare service based on a particular multiplier value associated with the particular healthcare facility; and
causing display of a visualization indicative of the particular cost estimate relative to a displayed map of a geographic region.

16. The method of claim 15, wherein the particular cost estimate belongs to a plurality of cost estimates each associated with a visualization element indicating that the cost estimate as low for the geographic region, typical for the geographic region, or high for the geographic region.

17. The method of claim 15, comprising:
causing display of a plurality of visualization elements associated with a plurality of cost estimates for the particular healthcare service, wherein each visualization element represents a different insurer;
causing display of information related to a cost estimate of a selected insurer.

18. The method of claim 15, comprising:
causing display of a customizable cost estimate based on additional user input.

19. The method of claim 15, wherein the visualization includes a range of cost estimates for an insurer as a function of a plurality of healthcare facilities, wherein the cost estimates are ranked and color coded to indicate a relative cost.

20. A computer system comprising:
a processor; and
memory including instructions that, when executed by the processor, cause the computer system to:
obtain private healthcare insurance claims data and public healthcare fee schedule data from one or more data sources;
generate a model based on training data including a combination of the private healthcare insurance claims data and the public healthcare fee schedule data; and
determine a multiplier for each of the plurality of healthcare facilities based on the model, wherein a multiplier associated with a healthcare facility is indicative of a value used to scale the public healthcare fee schedule for the healthcare facility such that a cost for a healthcare service associated with the healthcare facility is estimated based on the multiplier of the healthcare facility.

21. The system of claim 20, the memory further comprising instructions that, when executed by the processor, cause the computer system to:
process receipt of a query to estimate a cost of a particular healthcare service performed at a particular healthcare facility;
calculate a particular cost estimate for the particular healthcare service based on a particular multiplier value associated with the particular healthcare facility; and
cause display of the cost estimate or data indicative of the cost estimate for the particular healthcare service.

22. The system of claim 21, wherein the model defines a plurality of episodes of care, each having a frequency weighted combination of the particular healthcare service and at least one additional healthcare service, and the particular of cost estimate is based on a normalized aggregate of costs for the services including in the plurality of episodes of care.

23. The system of claim 21, the memory further comprising instructions that, when executed by the processor prior to calculating the particular cost estimate, cause the computer system to:
receive user input indicating a geographic region, wherein the query for the particular cost estimate is constrained by the geographic region such that the particular cost estimate is constrained to the geographic region.

24. The system of claim 21, the memory further comprising instructions that, when executed by the processor prior to calculating the particular cost estimate, cause the computer system to:
receive user input indicating a particular insurer, wherein the query for the cost estimate is constrained by the insurer such that the particular cost estimate is constrained to the insurer.

25. A non-transitory machine-readable storage medium storing instructions, an execution of which in a computer system causes the computer system to perform operations comprising:
obtaining private healthcare insurance claims data and public healthcare fee schedule data from one or more data sources;
generating a model based on training data including a combination of the private healthcare insurance claims data and the public healthcare fee schedule data; and
determining a multiplier for each of the plurality of healthcare facilities based on the model, wherein a multiplier associated with a healthcare facility is indicative of a value used to scale the public healthcare fee schedule for the healthcare facility such that a cost for a healthcare service associated with the healthcare facility is estimated based on the multiplier of the healthcare facility.

* * * * *